US006486088B1

(12) United States Patent
Crowther et al.

(10) Patent No.: US 6,486,088 B1
(45) Date of Patent: Nov. 26, 2002

(54) HIGH ACTIVITY CARBENIUM-ACTIVATED POLYMERIZATION CATALYSTS

(75) Inventors: Donna Jean Crowther, Seabrook, TX (US); Bernard Jean Folie, Lasne (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/694,142

(22) Filed: Oct. 23, 2000

Related U.S. Application Data

(63) Continuation-in-part of application No. 09/422,533, filed on Oct. 21, 1999, now Pat. No. 6,300,433.
(60) Provisional application No. 60/105,329, filed on Oct. 23, 1998.

(51) Int. Cl.$^7$ ................................................ B01J 31/14
(52) U.S. Cl. ....................... 502/103; 526/120; 526/126; 526/127; 526/134; 526/943; 502/152
(58) Field of Search ................................ 526/120, 126, 526/127, 134; 502/103, 152

(56) References Cited

U.S. PATENT DOCUMENTS

| | | |
|---|---|---|
| 4,463,135 A | 7/1984 | Maly |
| 4,543,399 A | 9/1985 | Jenkins, III et al. |
| 4,588,790 A | 5/1986 | Jenkins, III et al. |
| 5,001,205 A | 3/1991 | Hoel |
| 5,028,670 A | 7/1991 | Chinh et al. |
| 5,153,157 A | 10/1992 | Hlatky et al. |
| 5,198,401 A | 3/1993 | Turner et al. |
| 5,241,025 A | 8/1993 | Hlatky et al. |
| 5,278,119 A | 1/1994 | Turner et al. |
| 5,296,433 A | 3/1994 | Siedle et al. |
| 5,324,800 A | 6/1994 | Welborn, Jr. et al. |
| 5,352,749 A | 10/1994 | DeChellis et al. |
| 5,382,638 A | 1/1995 | Bontemps et al. |
| 5,387,568 A | 2/1995 | Ewen et al. |
| 5,405,922 A | 4/1995 | DeChellis |
| 5,408,017 A | 4/1995 | Turner et al. |
| 5,427,991 A | 6/1995 | Turner |
| 5,436,304 A | 7/1995 | Griffin et al. |
| 5,447,895 A | 9/1995 | Marks et al. |
| 5,453,471 A | 9/1995 | Bernier et al. |
| 5,462,999 A | 10/1995 | Griffin et al. |
| 5,483,014 A | 1/1996 | Turner et al. |
| 5,610,115 A | 3/1997 | Soga et al. |
| 5,635,573 A | 6/1997 | Harrington et al. |
| 5,688,634 A | 11/1997 | Mixon et al. |
| 5,763,556 A | 6/1998 | Shaffer et al. |
| 5,767,208 A | 6/1998 | Turner et al. |
| 5,895,771 A | 4/1999 | Epstein et al. |
| 5,939,347 A | 8/1999 | Ward et al. |

FOREIGN PATENT DOCUMENTS

| | | |
|---|---|---|
| EP | 0 426 638 A | 5/1991 |
| EP | 0 426 638 B | 4/1996 |
| EP | 0 708 117 A | 4/1996 |
| EP | 0786466 A1 * | 7/1997 |
| EP | 0 786 466 A | 7/1997 |
| EP | 0 612 768 B | 11/1997 |
| EP | 0 824 113 A | 2/1998 |
| WO | WO 95/29940 A | 11/1985 |
| WO | WO 92/00333 | 1/1992 |
| WO | WO 91/09882 | 7/1992 |
| WO | WO 92/14766 | 9/1992 |
| WO | WO 93/02099 | 2/1993 |
| WO | WO 93/11172 | 6/1993 |
| WO | WO 93/14132 | 7/1993 |
| WO | WO 94/03506 | 2/1994 |
| WO | WO 95/07941 | 3/1995 |
| WO | WO 95/07942 | 3/1995 |
| WO | WO 96/28480 | 9/1996 |
| WO | WO 96/33227 | 10/1996 |
| WO | WO 96/35726 | 11/1996 |
| WO | WO 97/22635 A | 6/1997 |
| WO | WO 97/22635 | 6/1997 |
| WO | WO 97/22639 | 6/1997 |
| WO | WO 97/29845 | 8/1997 |
| WO | WO 98/37106 | 8/1998 |
| WO | WO 98/41530 | 9/1998 |
| WO | WO 98/55518 | 12/1998 |
| WO | WO 99/06135 | 2/1999 |
| WO | WO 99/30822 | 6/1999 |
| WO | WO 99/42467 | 8/1999 |
| WO | WO 99/43717 | 9/1999 |
| WO | WO 99/45040 | 9/1999 |
| WO | WO 99/45042 | 9/1999 |

OTHER PUBLICATIONS

"Novel Transition Metal Compounds for Polymerization of Olefins with Improved Efficiency and Polymerization of Olefins Using Them", Inoe, Norihide, et al., Chemical Abstracts, vol. 24, No. 14, (Apr. 1, 1996), Abstract No. 177218 and JP 07 247309–Abstract.
Chem. Rev., 1993, v.93(3), pp. 927–942—"The Search for Larger and More Weakly Coordinating Anions"—Steven H. Strauss.
Acc. Chem. Res., 1998, v.31, pp. 133–139—Christopher A. Reed—"Carboranes: A New Class of Weakly Coordinating Anions for Strong Electrophiles, Oxidants, and Superacids".
Macromol. Chem. Phys,. 1998, v.199, pp. 1135–1152—Michael Arndt, et al.,—Ethene/propene Copolymerization by [Me$_2$C(3–RCp)(Flu)]ZrCl$_2$/MAO (R=H, Me, $^{iso}$Pr, $^{tert}$Bu).

(List continued on next page.)

Primary Examiner—David W. Wu
Assistant Examiner—William K Cheung
(74) Attorney, Agent, or Firm—Charles E Runyan, Jr.

(57) ABSTRACT

This application discloses triphenyl carbenium NCA's as catalyst activators for a class of asymmetrically bridged hafnocene catalyst precursors. These catalsyst precursors are activated into olefin polymerization catalysts and are suitable for gas, solution, and slurry-phase polymerization reactions. The disclosed bridge is methylenyl- or silanylenyl-based and is optionally, alkyl or aryl substituted. The catalytic activity of the disclosed hafnocene catalyt precursors is substantially enhanced over identical catalysts that are activated with other activators.

17 Claims, No Drawings

OTHER PUBLICATIONS

"New Metallocenes . . . ", Tosoh Corp. *Metallocenes '95*, 1995, pp. 441–462.

*Macromol. Chem. Phys.* 1999, v.200, pp. 1542–1553—"Ethylene/1–hexene copolymerization with $Ph_2C(Cp)(Flu)ZrCl_2$ derivatives: correlation between ligand structure and copolymerization behavior at high temperature"—Akihiro Yano, et al.

"Synthesis and Applications of Metallocene–Based Elastomers", H. Miyata, et al., TOSOH Corp., Worldwide Metallocene Cenference, *MetCon '96*, Jun. 12–13, 1996, Houston, Texas.

USSN 09/042,378 filed Mar. 13, 1998.
USSN 08/999,214 filed Dec. 29, 1997.
USSN 09/261,627 filed Mar. 3, 1999.
USSN 60/087,447 filed Jun. 1, 1998.
USSN 09/277,339 filed Mar. 26, 1999.
USSN 09/092,752 filed Jun. 5, 1998.

Matsukawa, Tetsuya et al., "Manufacture of Stereospecific Vinyl Chloride–based Polymers" Abstract and JP 08 208736 A (Chisso Corp., Japan)—Aug. 13, 1996.

* cited by examiner

HIGH ACTIVITY CARBENIUM-ACTIVATED POLYMERIZATION CATALYSTS

RELATED APPLICATIONS

This application is a CIP of U.S. application Ser. No. 09/422,533, filed Oct. 21, 1999 U.S. Pat. No. 6,300,433 filed Oct. 9, 2001 and that claimed the benefit of U.S. prov. application Ser. No. 60/105,329, filed Oct. 23, 1998.

TECHNICAL FIELD

This invention relates to olefin copolymerization processes using substituted hafnocene catalyst compounds with noncoordinating anions.

BACKGROUND ART

Olefin polymers comprising ethylene and at least one or more α-olefin and optionally one or more diolefin make up a large segment of polyolefin polymers and will be addressed as "ethylene copolymers" herein. Such polymers range from crystalline polyethylene copolymers to largely amorphous elastomers, with a new area of semi-crystalline "plastomers" in between. In particular, ethylene copolymer plastomers are now a well established class of industrial polymers having a variety of uses associated with their unique properties, such as elastomeric properties and their thermo-oxidative stability. Uses of the plastomers include general thermoplastic olefins, films, wire and cable coatings, polymer modification (by inclusion in blends with other polyolefins), injection molding, foams, footwear, sheeting, functionalized polymers (such as by free-radical graft addition of polar monomers) and components in adhesive and sealant compounds.

Commercially prepared ethylene copolymers have been traditionally been made via Ziegler-Natta polymerization with catalyst systems largely based on vanadium or titanium. Newer metallocene catalyst compounds have received attention due to their ease of larger monomer incorporation and potential increases in polymerization activities. U.S. Pat. No. 5,324,800 describes metallocenes having substituted and unsubstituted cyclopentadienyl ligands which are suitable for producing high molecular weight olefin polymers, including linear, low density copolymers of ethylene with minor amounts of α-olefin.

Additionally, polypropylene is an important industrial polymer. To the extent that catalysts for these polymerizations can be improved, their use provides economic benefit.

Noncoordinating anions useful as catalyst components with such metallocenes are known. The term "noncoordinating anion" is now accepted terminology in the field of olefin polymerization, both by coordination or insertion polymerization and carbocationic polymerization. The noncoordinating anions function as electronic stabilizing cocatalysts, or counterions, for cationic metallocenes which are active for olefin polymerization. The term "noncoordinating anion" as used here and in the references applies both to noncoordinating anions and weakly coordinating anions that are not so strongly coordinated to the cationic complex as so to be labile to replacement by olefinically or acetylenically unsaturated monomers at the insertion site. U.S. Pat. No. 5,198,401 describes a preferred noncoordinating anion tetra(perflourophenyl)boron, $[B(pfp)_4]$- or $[B(C_6F_5)_4]$-, wherein the perfluorinated phenyl ligands on the boron makes the counterion labile and stable to potential adverse reactions with the metal cation complexes.

The utility of metallocene-based ionic catalysts in high temperature olefin polymerization is described in U.S. Pat. Nos. 5,408,017 and 5,767,208, EP 0 612 768, and WO 96/33227. Each addresses suitable metallocene catalysts for high temperature processes for olefin copolymerization. High molecular weight ethylene/α-olefin copolymers is an objective of EP 0 612 768 and is addressed with catalyst systems based on bis(cyclopentadienyl/indenyl/fluorenyl) hafnocenes which are combined with an alkyl aluminum compound and an ionizing ionic compound providing a non-coordinating anion.

Improved catalyst systems for olefin polymerization are industrial useful.

BRIEF SUMMARY

The invention thus addresses specifically substituted, bridged hafnocene catalyst complexes activated with cocatalysts in which specific choices of catalyst and activator lead to unexpectedly high catalysis activities such that olefin cpolymers and copolymers can be prepared at surprisingly high production rates. More specifically, the invention relates tocatalysts for polymerizing olefins under supercritical or solution polymerization conditions at a reaction temperature at, or above, 60° C. to 225° C., or below. Specific monomers useful in the invention include ethylene and/or propylene and one or more comonomers capable of insertion polymerization with a hafnocene catalyst complex derived from A) a biscyclopentadienyl hafnium organometallic compound having i) at least one unsubstituted cyclopentadienyl ligand or aromatic fused-ring substituted cyclopentadienyl ligand not having additional substitutents on said ligand, ii) one substituted or unsubstituted, aromatic fused-ring substituted cyclopentadienyl ligand, and iii) a covalent bridge connecting the two cyclopentadienyl ligands where the bridge has a single carbon or silicon atom plus additional moieties that complete carbon or silicon's valence; and B) an activating cocatalyst, preferably a precursor ionic compound comprising a halogenated tetraaryl-substituted Group 13 anion and a carbenium cation.

DEFINITIONS

Carbenium cations are cations in which carbon has a formal valence of 3 leaving it with a +1 charge. Such a species is highly lewis acidic and is a useful metallocene activator. Isoelectronic or isostructural cations in which the carbon is replaced with for example Si are also useful.

Cyclopentadienyl ligands: Cyclopentadienyl ligands are those ligands that have a cyclopentadiene anion core. These can be unsubstituted or substituted with hydrocarbyl groups as defined below. They can be part of fused-ring systems such as indenyl and fluorenyl. Similarly the use of heteroatom containing cyclopentadienyl rings or fused rings, where a non-carbon Group 14, 15 or 16 atom replaces one of the ring carbons in the cyclopentadienyl ring or in a ring fused with the cyclopentadienyl ring is within the scope of cyclopentadienyl. The important component of a cyclopentadienyl ligand for this disclosure is that the ligand retain the aromatic, substantially planar, five-membered ring of the cyclopentadienide anion. The terms "indenyl" and "fluorenyl" ligands are therefore within the scope of cyclopentadienyl. When this disclosure wishes to refer to cyclopentadienide itself, it uses cyclopentadienide or cyclopentadine anion. See, for example, the teachings of WO 98/37106 common priority with U.S. Ser. No. 08/999,214, filed Dec. 12, 1997 pending allowed and WO 98/41530, having common priority with U.S. Ser. No. 09/042,378, filed Mar. 13, 1998 abandoned Dec. 1, 1999 incorporated by reference for purposes of U.S. patent practice.

Cyclopentadienyl substitutions R and R', typically include one or more $C_1$ to $C_{30}$ hydrocarbon or hydrocarbylsilyl groups selected from linear, branched, cyclic, aliphatic, aromatic or combined structure groups, including fused-ring or pendant configurations. Examples include methyl, isopropyl, n-propyl, n-butyl, isobutyl, tertiary butyl, neopentyl, phenyl, n-hexyl, cyclohexyl, and benzyl.

T is a bridge with two aryl groups, each substituted with a $C_1$–$C_{20}$ hydrocarbyl or hydrocarbylsilyl group at least one of which is a linear $C_3$ or greater substitutent The bridge substituents preferably comprise $C_1$–$C_{20}$ linear or branched alkyl, or $C_1$–$C_{20}$ substituted-silyl, substituted phenyl groups, the alkyl or substituted-silyl substituents located in the para- or meta-positions of the aryl groups, preferably wherein at least one of said alkyl substituents is a $C_3$ or higher linear n-alkyl substitutent, preferably $C_4$ or higher. Specific examples include methyl, ethyl, n-propyl, n-butyl, sec-butyl, isobutyl, tert-butyl, n-pentyl, neopentyl, etc.

Q are hafnocene ligands that can be abstracted by the activator and are ligands that a olefin monomer can insert into as polymerization occurs. Q substituents specifically include fluorinated aryl groups, preferably perfluorinated aryl groups, and include substituted Q groups having substituents additional to the fluorine substitution, such as fluorinated hydrocarbyl groups. Preferred fluorinated aryl groups include phenyl, biphenyl, napthyl, and derivatives thereof. The disclosures of U.S. Pat. Nos. 5,198,401, 5,296, 433,5,278,119, 5,447,895, 5,688,634, 5,895,771, WO 93/02099, WO 97/29845, WO 99/43717, WO 99/42467 and copending U.S. application Ser. No. 09/261,627, filed Mar. 3, 1999 U.S. Pat. No. 6,262,202 Jul. 7, 2001 and its equivalent WO 99/45042 are particularly instructive as to suitable Q substituents and are incorporated by reference for purposes of U.S. patent practice.

Hydrocarbyl: For the purposes of this application the term "hydrocarbon" or "hydrocarbyl" is meant to include those compounds or groups that have essentially hydrocarbon characteristics but optionally contain not more than about 10 mol. % non-carbon atoms, such as boron, silicon, oxygen, nitrogen, sulfur and phosphorous. "Hydrocarbylsilyl" is exemplified by, but not limited to, dialkyl- and trialkylsilyls.

Alkyl is a radical based on an aliphatic hydrocarbon. This backbone can be substituted by any number of other alkyl or aryl substituents as is known in the art.

Aryl is a radical based on an aromatic hydrocarbon. This backbone can be substituted by any number of other aryl or alkyl substituents as is known in the art.

NCA Is a non-coordinating ion. This term encompasses anions that are coordinating but only weakly so. The key is that incoming olefin monomer is capable of replacing NCA during a polymerization process.

DETAILED DESCRIPTION

The bridged hafnium compounds of the invention include those having a single substituted carbon or silicon atom bridging two cyclopentadienyl-containing (Cp) ligands of the hafnium metal centers. The Cp ligands are either substituted or unsubstituted, preferrably substituted. The bridge is either methyleneyl or silylenyl-based and is substituted or unsubstituted, preferably substituted.

Specific bridged hafnium catalysts include those derived from: (1) indenyl-based complexes such as the isomers, or mixtures, of (para-n-butylphenyl) (para-t-butylphenyl) methylene(fluorenyl)(indenyl)hafnium dimethyl, (para-n-propylphenyl)(para-methylphenyl)methylene(fluorenyl)(indenyl)hafnium dimethyl, di(para-n-butylphenyl) methylene(2,7-di tertbutyl fluorenyl)(indenyl)hafnium dimethyl, (para-n-butylphenyl)(para-t-butylphenyl) methylene (2,7-di tertbutyl fluorenyl)(indenyl)hafnium dimethyl, (para-n-butylphenyl)(para-t-butylphenyl) methylene(2,7-dimethyl fluorenyl)(indenyl)hafnium dibenzyl and di(para-n-butylphenyl)methylene (fluorenyl)(indenyl)hafnium dimethyl; and, (2) fluorenyl-based complexes such as (para-n-propylphenyl)(para-i-propylphenyl)silyl(fluorenyl)(fluorenyl)hafnium di-t-butyl, di(para-n-propylphenyl)methylene(2,7-di-tert-butyl-5-methylfluorenyl) (fluorenyl)hafnium dimethyl; and (3) cyclopentadienyl-based complexes such as the isomers, or mixtures, of (para-n-propylphenyl)(para-i-propylphenyl) methylene (fluorenyl)(cyclopentadienyl)hafnium dimethyl, (para-n-butylphenyl)(para-t-butylphenyl)methylene (fluorenyl)(cyclopentadienyl)hafnium dimethyl, di(para-n-butylphenyl)methylene (2,7-di tertbutyl fluorenyl) (cyclopentadienyl)hafnium dimethyl, (para-n-butylphenyl) (para-t-butylphenyl)methylene(2,7-di tertbutyl fluorenyl) (cyclopentadienyl)hafnium dimethyl, and di(para-n-butylphenyl)methylene (2,7-dimethyl fluorenyl) (cyclopentadienyl)hafnium dimethyl or dibenzyl. It has been found that the substituted bridge-containing compounds, such as those asymmetric compounds listed above, are particularly useful in accordance with the invention.

The invention activating cocatalyst, precursor ionizing compounds comprise Group 13 element complexes having at least two halogenated aromatic ligands such as the halogenated tetraphenyl boron and aluminum compounds exemplified in the identified prior art.

Those anions with mixed ligands are also suitable. Tris (perfluorophenyl)(perfluoronapthyl)borate is an illustrative complex. Thus, generically speaking, the Group 13 complexes useful in a accordance with the invention will typically conform to the following formula:

$$[M(A)_{4-n}(C)_n]^-$$

where, M is a Group 13 element, A is an nonhindering ligand as described above, C is a hindering ligand, one having bulky substitutents on the closest aryl ring bonded to the metal/metalloid center other than those described as suitable above, and n=0, 1, or 2. See also copending application U.S. Ser. No. 60/087447, filed Jun. 1, 1998 and its equivalent WO 99/45042, the teachings of which are referred to and incorporated by reference for purposes of U.S. patent practice.

For both fused aromatic rings and aromatic ring assemblies, the halogenation is highly preferred so as to allow for increased charge dispersion that contributes along with steric bulk as independent features decreasing the likelihood of ligand abstraction by the strongly Lewis acidic metallocene cation formed in the catalyst activation. Additionally, halogenation inhibits reaction of the hafnium cation with any remaining carbon-hydrogen bonds of the aromatic rings, and perhalogenation precludes such potential undesirable reactions. Thus it is preferred that at least one third of hydrogen atoms on carbon atoms of the aryl ligands can be replaced by halogen atoms, and more preferred that the aryl ligands be perhalogenated. Fluorine is the most preferred halogen, perfluorinated aryl ligands are most preferred.

Means of preparing ionic catalyst systems comprising catalytically active cations of the hafnium compounds and suitable noncoordinating anions are conventionally known, see for example U.S. Pat. No, 5,198,401, WO 92/00333, WO 97/22639, and EP 0 612 768. Typically the methods comprise obtaining from commercial sources or synthesizing the selected transition metal compounds comprising an abstractable ligand, e.g., hydride, halide, alkyl, alkenyl or hydro-carbyl-silyl group, and contacting them with a non-coordinating anion source or suitable precursor compounds in a suitable solvent. The anion precursor compound abstracts a monoanionic ligand (or one monoanionic bond of bidentale alkenyl ligands) that completes the valency requirements of the preferred hafnium metallocene compounds. The abstraction leaves the hafnocenes in an essentially cationic state which is counterbalanced by the stable, compatible and bulky, noncoordinating anions according to the invention. Each of the documents of this paragraph are incorporated by reference for purposes of U.S. patent practice.

The noncoordinating anions are preferably introduced into the catalyst preparation step as ionic compounds having an essentially cationic complex which abstracts a non-cyclopentadienyl, labile ligand of the transition metal compounds which upon abstraction of the non-cyclopentadienyl ligand, leave as a by-product the noncoordinating anion portion. Hafnium compounds having labile hydride, alkyl, or silyl ligands on the metal center are highly preferred for the ionic catalyst systems of this invention since known in situ alkylation processes may result in competing reactions and interactions that tend to interfere with the overall polymerization efficiency under high temperature conditions in accordance with the preferred process embodiments of the invention.

Suitable cations for precursor compounds capable of providing the noncoordinating anions of the invention cocatalysts include those known in the art, in which the cation is a carbenium or an analog of carbenium. Such include the carbenium, oxonium or sulfonium cations of U.S. Pat. No. 5,387,568.

Examples of suitable anionic precursors include those comprising a stable carbenium ion, and a compatible noncoordinating anion. These include tropillium tetrakis (perfluoronapthyl) or tetrakis(perfluoro-4-biphenyl)borate, triphenylmethylium tetrakis(perfluoronapthyl) or tetrakis (perfluoro-4-biphenyl)borate, benzene(diazonium)tetrakis (perfluoronapthyl) or tetrakis(perfluoro-4-biphenyl)borate, tropillium tetrakis(perfluoronapthyl) or tetrakis(perfluoro-4-biphenyl)borate, triphenylmethylium tetrakis (perfluoronapthyl) or tetrakis(perfluoro-4-biphenyl)borate, benzene(diazonium)tetrakis(perfluoronapthyl) or tetrakis (perfluoro-4-biphenyl)orate, tropillium tetrakis (perfluoronapthyl) or tetrakis(perfluoro-4-biphenyl)borate, triphenylmethylium tetrakis(perfluoronapthyl) or tetrakis (perfluoro-4-biphenyl)borate, benzene(diazonium)tetrakis (perfluoronapthyl) or tetrakis(perfluoro-4-biphenyl)borate. The essentially structurally equivalent silylium borate or aluminate salts are similarly suitable.

The term "scavenger" as used in this application is used in its art-recognized sense of being sufficiently Lewis acidic to coordinate with polar contaminates and impurities adventiously occurring in the polymerization feedstreams or reaction medium. Such impurities can be inadvertently introduced with any of the polymerization reaction components, particularly with solvent, monomer and catalyst feed, and adversely affect catalyst activity and stability. In particular, for processes utilizing recycle streams of unconverted monomer for reprocessing, the necessity to use polar compounds as catalyst deactivators, or "killers", such as water or lower alcohols, effectively necessitates the use of scavengers, as does the natural occurrence of polar impurities in monomer feedstreams. It can result in decreasing or even elimination of catalytic activity, particularly when a metallocene cation-noncoordinating anion pair is the catalyst system. The polar impurities, or catalyst poisons include water, oxygen, metal impurities, etc. Preferably steps are taken before provision of such into the reaction vessel, for example by chemical treatment or careful separation techniques after or during the synthesis or preparation of the various components, but some minor amounts of scavenging compound will still normally be required in the polymerization process itself.

Typically the scavenging compound will be an organometallic compound such as the Group-13 organometallic compounds of U.S. Pat. No. 5,241,025, EP-A-0 426 638 and those of U.S. Pat No. 5,767,208. Exemplary compounds include triethyl aluminum, triethyl borane, tri-isobutyl aluminum, methylalumoxane, isobutyl aluminumoxane, tri-n-hexyl aluminum and tri-n-octyl aluminum, those having bulky substituents covalently bound to the metal or metalloid center being preferred to minimize adverse interaction with the active catalyst. Addition of excess scavenger causes lower productivity, molecular weight and comonomer incorporation. The aluminum to hafnium molar ratios (Al:Hf) should accordingly be less than about 100:1, preferably less than about 75:1, more preferably less than about 50:1, and most preferably less than about 30:1. Molar ratios of less than 20:1 and less than 15:1 have been observed to be sufficient for the continuous processes described in this application.

The preferred scavenger is a long chain, linear tri-alkyl aluminum compound, and that longer chains are preferred over shorter chains. See WO 97/22635 and U.S. Pat. No. 5,767,208 for further discussion, this document is incorporated by reference for purposes of U.S. patent practice. Non-limiting examples of effective long chain, linear tri-alkyl ligand-containing scavengers include those comprised in the group defined by the formula M'R'R"R'", where M' is Al, and each of the R groups independently is a $C_4$ or higher linear, branched or cyclic alkyl group, preferably $C_6$ or higher, most preferably $C_8$ or higher. The long chain, linear alkyl aluminums where each alkyl substituent was of a length of $C_8$ or higher, preferably $C_9$ and higher were observed to exhibit optimal performance, that defined as having the least deleterious effect when used at a level in excess of the optimum level as described in the following paragraph. Specifically included are: tri-n-octyl aluminum, tri-n-decyl aluminum, tri-n-dodecyl aluminum, tri-n-hexadecyl aluminum, and the higher carbon number equivalents, e.g., $(C_{20})_3$Al, including those with mixed ligation, and mixed scavenger compounds as well. The hydrolyzed derivatives of these alkyl-ligand containing organoaluminum compounds will additionally be suitable. Additionally, it will be apparent that those scavenging compounds comprising both long-chain, linear and bulky ligands or mixed linear ligands, each ligand as described above, will also be suitable, but perhaps less desirable due to more involved or expensive syntheses.

A preferred polymerization process is that designed or conducted such that the cocatalyst components, that is the transition metal compounds and the anion precursor compounds, are maintained separately until just prior to or during polymerization use in the chosen reactor or reactors. An example is the use of dual injection of each catalyst component directly into the reactor or the use of T- or multi-joint mixing chambers just prior to injection into the reactor. Additional optimization can be achieved when the scavenger compound is introduced into the reactor independently of the catalyst system or compounds, preferably after the activation of the hafnocenes with the anion precursor cocatalysts.

The process of the invention is applicable to high pressure homogeneous polymerization, preferably employing less than 30 wt % of solvent, which is substantially adiabatic and where the heat of polymerization is accommodated by a rise in temperature of the reactor contents instead of internal or external cooling. In this case, the contents consist principally of unreacted monomer. Such process may be performed, under a single or dual phase homogeneous conditions at pressures from 250 to 3000 bar, preferably from 500 to 2500 bar, with or without unreactive diluents or solvents at temperatures generally above the melting point of the polymer being produced. Such processes are industrially known and may include the use of scavenger compounds and catalyst deactivation or killing steps, see for example U.S. Pat. No. 5,408,017, WO 95/07941, and WO 92/14766. Each of these documents and their U.S. counterparts are incorporated by reference for purposes of U.S. patent practice. Preferred catalyst deactivators, or killers, include high molecular weight, non-recyclable compounds, such as poly vinyl alcohol which exhibit the functional capacity to complex with the catalysts so as to deactivate them while not forming volatile polar by-products or residual unreacted compounds.

The process of the invention is also especially applicable to homogeneous solution polymerization which is also substantially adiabatic, that is to say the heat of polymerization is accommodated by a rise in temperature of the polymerization reactor contents, here principally solvent. This adiabatic process typically would have no internal cooling and suitably no external cooling. The reactor outlet stream removes the heat of polymerization from the reactor. The productivity of such adiabatic processes can be improved by cooling the inlet solvent and/or monomer stream(s) prior to introduction into the reactor to permit a greater polymerization exotherm. Thus the catalyst, cocatalyst and scavenger selections disclosed in this application can be advantageously practiced in a continuous, solution process operated at or above 140° C., above 150° C. or above 160° C., up to about 225° C. Most preferably the solution polymerization process for semi-crystalline polymers operated at a temperature from 140° C. –220° C. Typically this process is conducted in an inert hydrocarbon solvent, linear, cyclic or branched aliphatic, or aromatic, at a pressure of from 20 to 200 bar.

The α-olefins suitable for use in the preparation of the ethylene copolymers, or for the polyethylene copolymers, are preferably $C_3$ to $C_{20}$ α-olefins, but will include higher carbon number olefins such as polymerizable macromers having up to five hundred carbon atoms, or more. Illustrative non-limiting examples of such α-olefins are one or more of propylene, 1-butene, 1-pentene, 1-hexene, 1-octene, and 1-decene. Included in the term olefins for the purposes of describing effectively copolymerized monomers are the constrained-ring cyclic monoolefins such as cyclobutene, cyclopentene, norbornene, alkyl-substituted norbornes, alkenyl-substituted norbornenes, and the higher carbon number cyclic olefins known in the art, see U.S. Pat. No. 5,635,573, incorporated herein by reference for purposes of U.S. patent practice, and known copolymerizable diolefins, e.g., 1,4-hexadiene, ethylidene-norbornene, and vinyl-norbornene. Vinyl aromatic monomers, e.g., styrene and alkyl-substituted styrene monomers are additionally suitable. The polyethylene copolymers can range from semicrystalline to substantially amorphous; and will typically have a substantially random arrangement of at least the ethylene and the olefin comonomers. As will also be apparent to those skilled in the art, the use of asymmetrically substituted hafnium compounds of the invention enable the preparation of syndiotactic polymers from prochiral olefins, e.g., like propylene. Processes for such will also benefit from the increased productivity and molecular weights described here for ethylene copolymers.

The effective Group 8–15 element cocatalyst complexes of the invention are, in a preferable embodiment, derived from an ionic salt, comprising a 4-coordinate Group 10–14 element anionic complex, where A⁻ can be represented as:

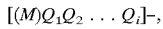

$[(M)Q_1Q_2 \ldots Q_i]^-$, where M is one or more Group 10–15 metalloid or metal, preferably boron or aluminum, and either each Q is ligand effective for providing electronic or steric effects rendering $[(M')Q_1Q_2 \ldots Q_n]^-$ suitable as a noncoordinating anion as that is understood in the art, or a sufficient number of Q are such that $[(M')Q_1Q_2 \ldots Q_n]^-$ as a whole is an effective noncoordinating or weakly anion.

Additional suitable anions are known in the art and will be suitable for use with the metallocene catalysts of the invention. See U.S. Pat. No. 5,483,014, weakly coordinating anions from borane, carborane, borate, carborate, metalloborane, or metallocarborane complexes are described and exemplified. See also, the review articles by S. H. Strauss, "The Search for Larger and More Weakly Coordinating Anions", *Chem. Rev.*, 93, 927–942 (1993) and C. A. Red, "Carboranes: A New Class of Weakly Coordinating Anions for Strong Electrophiles, Oxidants and Superacids", *Acc. Chem. Res.*, 31, 133–139 (1998).

In particular embodiments one Q group, or ligand, of the anionic complex may also be bonded to a. metal/metalloid oxide support or polymeric support. See, for example, U.S. Pat. Nos. 5,427,991 and 5,939,347, each incorporated by reference for purposes of U.S. patent practice. Metal or metalloid oxide supports of the described bonding method for the invention include any metal/metalloid oxides, preferably those having surface hydroxyl groups exhibiting a pKa equal to or less than that observed for amorphous silica, i.e., pKa less than or equal to about 11. Accordingly, any of the conventionally known silica support materials that retain hydroxyl groups after dehydration treatment methods will be suitable in accordance with the invention. Because of availability, both of silica and silica containing metal oxide based supports, for example, silica-alumina, are preferred. Silica particles, gels, and glass beads are most typical.

Polymeric supports are preferably hydroxyl-functional-group-containing polymeric substrates, but functional groups may be any of the primary alkyl amines, secondary alkyl amines, and others, where the groups are structurally incorporated in a polymeric chain and capable of a acid-base reaction with the Lewis acid such that a ligand filling one coordination site of the Group 13 element is protonated and replaced by the polymer incorporated functionality. See, for example, the functional group containing polymers of U.S. Pat. No. 5,288,677, the functionalized polymers of U.S. Pat. No. 5,427,991 and the descriptions in copending applications U.S. Ser. No. 09/277,339, filed Mar. 26 1999 pending and its equivalent PCT/99US/06135, and U.S. Ser. No. 09/092,752, filed Jun. 5, 1998 U.S. Pat. No. 6,100,214 Aug. 8, 2000 and its equivalent WO 98/55518. All are incorporated by reference for purposes of U.S. patent practice.

Other known methods for supporting catalyst systems comprising a noncoordinating anion cocatalyst will also be suitable as means for supporting the catalyst complexes of this invention. Thus, the catalyst complexes of the invention may also physically deposited on or affixed to a suitable support material. See, for example, the teachings of WO 91/09882, WO 93/11172, WO 96/35726 and U.S. Pat. Nos. 4,463,135, and 5,610,115.

When using the above catalysts, the catalyst system will generally employ one or more scavenging agents to remove polar impurities from the reaction environment and to increase catalyst activity. Any polymerization-reaction components, particularly solvents, monomers, and catalyst feeds, can inadvertently introduce impurities and adversely affect catalyst activity and stability. Impurities decrease or even eliminate catalytic activity, particularly with ionizing-anion-activated catalyst systems. Polar impurities, or catalyst poisons, include water, oxygen, metal impurities, etc. Preferably, these impurities are removed from or reduced in the reaction components before their addition to the reaction vessel. Impurities can be removed by chemically treating the components or by impurity separation steps. Such treatment or separation can occur during or after synthesis of the components. In any case, the polymerization process will normally employ minor amounts of scavenging agent. Typically, these scavengers will be organometallic such as the Group-13 compounds of U.S. Pat, Nos. 5,153,157, 5,241,025 and WO-A- 91/09882, WO-A-94/03506, WO-A-93/14132, and that of WO 95/07941. Exemplary compounds include triethyl aluminum, triethyl borane, triisobutyl aluminum, methylalumoxane, and isobutyl alumoxane. Those compounds having bulky or $C_6$–$C_{20}$ linear hydrocarbyl substituents covalently bound to the metal or metalloid center are preferred because they coordinate to the active catalyst more weakly. Examples include triethylaluminum, but more preferably, bulky compounds such as triisobutylaluminum, triisoprenylaluminum, and long-chain, linear-alkyl-substituted aluminum compounds, such as tri-n-hexylaluminum, tri-n-octylaluminum, or tri-n-dodecylaluminum. When alumoxane is used as activator, any excess over that needed to activate the catalyst can act as a scavenger and additional organometallic scavengers may be unnecessary. Alumoxanes also may be used as scavengers with other activators, e.g., methylalumoxane and triisobutyl-alumoxane with boron-based activators. The scavenger amount is limited to that amount effective to enhance activity (and with that amount necessary for activation when used in a dual role) since excess amounts may act as catalyst poisons.

This invention's catalyst system can polymerize those unsaturated monomers conventionally recognized as polymerizable using metallocenes. Typical conditions include solution, slurry, gas-phase, and high-pressure polymerization. The catalysts may be supported on inorganic oxide or polymeric supports and as such will be particularly useful in those operating modes employing fixed-bed, moving-bed, fluid-bed, slurry, or solution processes conducted in single, series, or parallel reactors. Invention cocatalysts may also function in catalyst pre-polymerization. WO 98/55518, incorporated by reference for purpose of U.S. patent practice, describes a preferred invention support method for gas-phase or slurry polymerization.

Alternative embodiments of this invention's olefin polymerization methods employ the catalyst system in liquid phase (solution, slurry, suspension, bulk phase, or combinations thereof), in high-pressure liquid or supercritical al fluid phase, or in gas phase. These processes may also be employed in singular, parallel, or series reactors. The liquid processes comprise contacting olefin monomers with the catalyst system described above in a suitable diluent or solvent and allowing those monomers to react long enough to produce the invention polymers. The term polymer encompasses both homo- and co-polymers. Both aliphatic and aromatic hydrocarbyl solvents are suitable; hexane is preferred. In bulk and slurry processes, the supported catalysts typically contacts a liquid monomer slurry. Gas-phase processes typically use a supported catalyst and follow any manner suitable for ethylene polymerization. Illustrative examples may be found in U.S. Pat. Nos. 4,543,399, 4,588, 790, 5,028,670, 5,382,638, 5352,749, 5,408,017, 5,436,304, 5,453,471, and 5,463,999, 5,767,208 and WO 95/07942. Each is incorporated by reference for purposes of U.S. patent practice. The minimum polymerization reaction temperature is about 40° C. Preferably, the minimum reaction temperature is about 60° C. The temperature can go as high as about 250° C., but preferably does not exceed 220° C. The minimum reaction pressure is about 1 mm Hg, preferably about 0.1 bar, and most preferably 1.0 bar. The maximum pressure is less than or equal to about 2500 bar, preferably 1600 bar or lower, but most preferably 500 bar or less.

Invention catalysts can produce several types of linear polyethylene including high- and ultra-high-molecular-weight polyethylenes, including both homo- and copolymers with other alpha-olefin monomers or alpha-olefinic or non-conjugated diolefins, e.g. $C_3$–$C_{20}$ olefins, diolefins, or cyclic olefins. The polyethylenes are produced by adding ethylene, and optionally one or more other monomers, with invention activated catalysts that have been slurried with a solvent, such as hexane or toluene, to a reaction vessel under low pressure (typically <50 bar), at a typical temperature of 40–250° C. Cooling typically removes polymerization heat. Gas-phase polymerization can be conducted, for example, in a continuous fluid-bed, gas-phase reactor operated at a minimum of 2000 kPa and up to 3000 kPa. The minimum temperature is 60° C.; the maximum temperature is 160° C. The gas-phase reaction uses hydrogen as a reaction modifier at a concentration of no less than 100 PPM. The hydrogen gas concentration should not exceed 200 PPM. The reaction employs a $C_4$–$C_8$ comonomer feedstream and a $C_2$ feedstream. The $C_4$–$C_8$ feedstream goes down to 0.5 mol %. It also may go up to 1.2 mol %. Finally, the $C_2$ feedstream has a minimum concentration of 25 mol %. Its maximum concentration is 35 mol %. See, U.S. Pat. Nos. 4,543,399, 4,588,790, 5,028,670 and 5,405,922 and 5,462,999, which are incorporated by reference for purposes of U.S. patent practice.

High-molecular-weight, low-crystallinity, ethylene-α-olefin elastomers (including ethylene-cyclic-olefin and ethylene-α-olefin-diolefin elastomers) can be prepared using catalysts activated by this inventions activators under traditional solution polymerization processes or by introducing ethylene gas into invention catalyst slurries with α-olefin, cyclic olefin, or either or both mixed with other polymerizable and non-polymerizable diluents. Typical ethylene pressures range from about 10 to about 1000 psig (69–6895 kPa) and the diluent temperature typically remains between about 40 and about 160° C. The process can occur in one or more stirred tank reactors, operated individually, in series, or in parallel. See the general disclosure of U.S. Pat. No. 5,001, 205 for general process conditions. See also, international application WO 96/33227 and WO 97/22639. All documents are incorporated by reference for purposes of US patent practice.

Besides those specifically described above other monomers may be polymerized using the invention's catalyst systems, for example, styrene, alkyl-substituted styrenes, isobutylene and other geminally disubstituted olefins, ethylidene norbornene, norbornadiene, dicyclopentadiene, and other olefinically-unsaturated monomers, including other cyclic olefins, such as cyclopentene, norbornene, alkyl-substituted norbornenes, and vinyl-group-containing, polar monomers capable of coordinating polymerization. See, for example, U.S. Pat. Nos. 5,635,573, 5,763,556, and WO 99/30822. Additionally, α-olefin macromonomers of up to 1000 mer units or more may be copolymerized yielding branched olefin polymers. Additionally, oligomerization, dimerization, hydrogenation, olefin/carbon-monoxide copolymerization, hydroformulation, hydrosilation, hydroamination, and related catalytic reactions catalyzed by activated cation complexes can be activated with invention cocatalyst activators.

The invention activators can be used to activate catalysts as described above individually for coordination polymerization or can activate mixed catalysts for polymer blends. Adept monomers and catalyst selection yields polymer blends analogous to those using individual catalyst compositions. Polymers having increased MWD for improved processing and other traditional benefits available from polymers made with mixed catalyst systems can be achieved using invention cocatalysts.

Blended polymer formation can be achieved ex situ through mechanical blending or in situ through using mixed catalyst systems. It is generally believed that in situ blending provides a more homogeneous product and allows the blend to be produced in one step. In-situ blending with mixed catalyst systems involves combining more than one catalyst in the same reactor to simultaneously produce multiple, distinct polymer products. This method requires additional catalyst synthesis, and the various catalyst components must be matched for their activities, the polymer products they generate at specific conditions, and their response to changes in polymerization conditions. Invention cocatalyst activators can activate mixed catalyst systems.

Ethylene-α-olefin (including ethylene-cyclic olefin and ethylene-α-olefin-diolefin) elastomers of high molecular weight and low crystallinity can be prepared using the invention catalysts under traditional solution polymerization conditions or by introducing ethylene gas into a slurry of polymerization diluent and catalyst. The polymerization diluent contains α-olefin monomers, cyclic olefin monomers, or their mixtures with other polymerizable and non-polymerizable monomers. In this case, polymerization reaction pressure varies, as well. The minimum pressure is 0.0013 bar; a pressure of at least 0.1 bar is more preferred. Most preferably, the reaction pressure is at least 1.0 bar. The maximum pressure is 2500 bar, with a pressure at most 1600 bar being preferred. The most preferred maximum pressure is 500 bar. Typical ethylene pressures will be between 10 and 1000 psig (69–6895 kPa) and the polymerization diluent temperature will typically be between −10 and 160° C. The process can use a stirred-tank reactor, or more than one reactor operated in series or parallel. See the general disclosure of U.S. Pat. No. 5,001,205, which is incorporated by reference for its description of polymerization processes, ionic activators, and useful scavenging compounds.

Slurry or gas-phase reaction processes can use pre-polymerization of the supported invention catalyst to further control polymer particle morphology, as is known in the art. For example, such reaction can be accomplished by pre-polymerizing a $C_2$–$C_6$ α-olefin for a limited time. Ethylene contacts the supported catalyst at between −15° to 30° C. and ethylene pressure of up to 250 psig (1724 kPa) for 75 min to obtain a polyethylene coating on the support (30,000–150,000 molecular weight). The above polymerization process can then use the pre-polymerized catalyst. Additionally, polymeric resins may be used as a support coating, typically by suspending a support in dissolved polystyrene resin or similar material followed by separation and drying.

The invention catalyst compositions can be used individually as described above or can be mixed with other known polymerization catalysts to prepare polymer blends. Monomer and catalyst selection allows polymer blend preparation under conditions analogous to those using individual catalysts. polymers having increased MWD for improved processing and other traditional benefits available from polymers made with mixed catalyst systems can thus be achieved.

EXAMPLES

All batch polymerization reactions were run using the following procedure. At room temperature, the 0.5 L reactor was charged with 250 ml dry hexane, 18 ml (14g) 1-octene and 8 micro liters TOA (25 wt % in hexane). The reactor was heated to 140 degrees C. and pressurized with ethylene to 265 psi. The ethylene partial pressure was kept constant during the polymerization by a pressure regulator. A catalyst solution, preactivated by mixing a one to one molar ratio of hafnocene to activator in toluene, was pumped into the reactor at a rate to maintain a small ethylene uptake and keep the temperature at 140–41 degrees C. After 20 minutes the ethylene pressure was vented and the reactyore contenes cooled and solvents removed to yield the polymer.

Example 1

This reaction employed diphenyl-methylene (cyclopentadienyl)(fluorenyl)hafnium dimethyl as the catalyst precursor, with a dimethylaniliniumtetrakis (pentafluorophenyl)borate activator. The reaction was run substantially as described above. The average activity for this run was 246 grams polymer/gram catalyst.

Example 2

This reaction employed dimethylsilanylenyl-bis(indenyl) hafnium di methyl as the catalyst precursor and dimethylaniliniumtetrakis(pentafluorophenyl)borate as the activator. Average activity was approximately 3200 grams polymer/gram catalyst.

Example 3

This reaction employed diphenyl-methylene (cyclopentadienyl)(fluorenyl)hafnium dimethyl as the catalyst precursor and triphenylmethylium tetrakis(perfluoro) borate as the activator. The average activity was 1250 grams of polymer/gram catalyst. The reaction was run as spelled out above.

As can be seen by comparing Example 1 (comparative) to Example 3, using triphenylcarbenium cations in the catalyst precursor results in a 3–5-fold increase in catalyst activity. Similar results were seen when the catalyst precursor is dimethylsilanylenyl-bis(indenyl)hafnium dimethyl.

What is claimed is:

1. A metallocene catalyst system comprising an ion pair formed by contacting a metallocene and an activator wherein:

(a) the metallocene is described by the formula

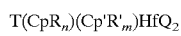

wherein
(i) Cp and Cp' are cyclopentadienyl ligands;
(ii) Each R and R' are the same or different hydrocarbyl radicals having 1–20 carbon atoms;
(iii) T is a bridge between Cp and Cp', and comprises a substituted or unsubstituted methylene or silylene radical;

(iv) each Q is a hydrocarbyl radical having 1–20 carbon atoms or is a halogen;
(v) n is the number of hydrocarbyl substituents on Cp and n=0–4;
(vi) m is the number of hydrocarbyl substituents on Cp' and m=0–4; and (b) the activator is described by the formula:

[Ar₃C][NCA]

wherein
(i) Ar is an aryl ligand;
(ii) Ar₃C is a triarylcarbenium; and
(iii) NCA is a non-coordinating anion.

2. The metallocene catalyst system of claim 1 wherein Cp, Cp', R, R', m and n are selected such that CpR$_m$ is not equal to Cp'R'$_n$.

3. The catalyst system of claim 1, wherein the non-coordinating anion is A(Ph*)₃X wherein
A is a Group-13 metalloid;
Ph* is pentafluorophenylene radical
X is alkyl-, alkylsily-, or halide-substituted phenyl or unsubstituted phenyl.

4. The catalyst system of claim 3 wherein A is boron.

5. The catalyst system of claim 1 wherein R$_m$ is selected such that CpR$_m$ forms a fluorenyl or indenyl radical.

6. The catalyst system of claim 5 wherein the fluorenyl radical is disubstituted with t-butyl radicals.

7. The catalyst system of claim 5 wherein R$_n$ is selected such that CpR$_n$ forms a substituted or unsubstituted cyclopentadienide radical.

8. The catalyst system of claim 1 wherein T is CZZ' or SiZZ' wherein Z and Z' are independently selected from substituted or unsubstituted, alkyl or aryl moieties.

9. The catalyst system of claim 8 wherein Z and Z' are independently selected from trialkyl-substituted phenyl moieties.

10. The catalyst system of claim 8 wherein Z and Z' are independently selected from phenyl and 4-(triethylsilanyl)phenyl.

11. The catalyst system of claim 10 wherein Z and Z' is phenyl.

12. The catalyst system of claim 10 wherein Z and Z' are 4-(triethylsilanyl)phenyl.

13. A metallocene catalyst system comprising an ion pair formed by contacting a metallocene and an activator wherein the metallocene has either formula I, II, or III and the activator has formula IV:

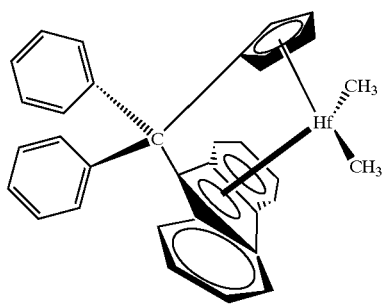

I

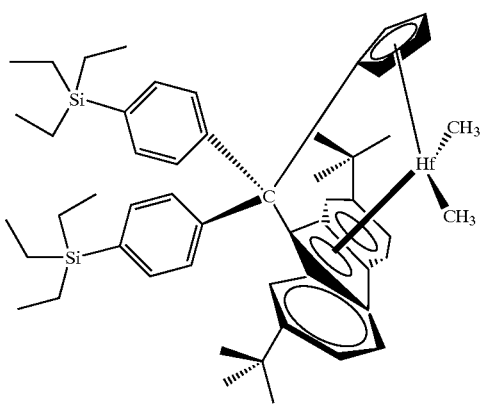

II

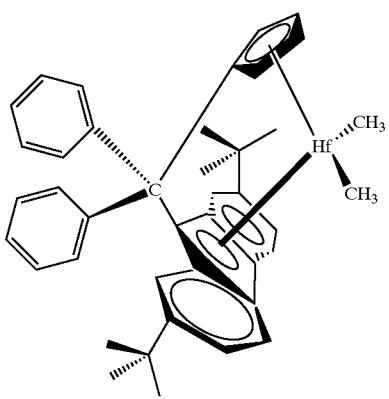

III

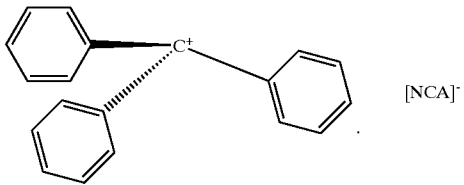

IV

14. A metallocene catalyst system comprising an ion pair formed by contacting diphenyl-methylene(cyclopentadienyl)(fluorenyl)hafnium dimethyl and triphenylcarbenium tetra(perfluorophenyl)borate.

15. A metallocene catalyst system comprising an ion pair formed by contacting di(4-(triethylsilanyl)phenyl)methylene(cyclopentadienyl)(fluorenyl)hafnium dimethyl and triphenylcarbenium tetra(perfluorophenyl)borate.

16. A metallocene catalyst system comprising an ion pair formed by contacting diphenylmethylene(cyclopentadienyl)(2,7-di-t-butylfluorenyl)hafnium dimethyl and triphenylcarbenium tetra(perfluorophenyl)borate.

17. A metallocene catalyst system comprising an ion pair formed by contacting di(4-(triethylsilanyl)phenyl)(cyclopentadienyl)(2,7-di-t-butylfluorenyl)hafnium dimethyl and triphenylcarbenium tetra(perfluorophenyl)borate.

* * * * *